United States Patent
Horgan et al.

(10) Patent No.: US 11,540,698 B2
(45) Date of Patent: Jan. 3, 2023

(54) SYSTEM AND METHOD FOR TREATMENT OF GASTROESOPHAGEAL VARICES

(71) Applicant: Boston Scientific Scimed, Inc., Maple Grove, MN (US)

(72) Inventors: Fergal Horgan, Galway (IE); Marie Turkington, Galway (IE); Martyn Folan, Galway (IE); Thomas Keating, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 434 days.

(21) Appl. No.: 16/849,206

(22) Filed: Apr. 15, 2020

(65) Prior Publication Data
US 2020/0237196 A1 Jul. 30, 2020

Related U.S. Application Data

(63) Continuation of application No. 15/638,474, filed on Jun. 30, 2017, now Pat. No. 10,653,299.

(60) Provisional application No. 62/357,598, filed on Jul. 1, 2016.

(51) Int. Cl.
| | |
|---|---|
| *A61B 1/00* | (2006.01) |
| *A61B 17/22* | (2006.01) |
| *A61N 7/00* | (2006.01) |
| *A61N 7/02* | (2006.01) |
| *A61B 1/015* | (2006.01) |
| *A61B 8/00* | (2006.01) |

(Continued)

(52) U.S. Cl.
CPC ...... *A61B 1/00101* (2013.01); *A61B 1/00089* (2013.01); *A61B 1/00137* (2013.01); *A61B 1/00163* (2013.01); *A61B 1/015* (2013.01); *A61B 17/22004* (2013.01); *A61N 7/00* (2013.01); *A61N 7/02* (2013.01); *A61N 7/022* (2013.01); *A61B 8/46* (2013.01); *A61B 2017/00269* (2013.01); *A61B 2018/00029* (2013.01)

(58) Field of Classification Search
CPC ................ A61B 1/00101; A61B 1/00089
See application file for complete search history.

(56) References Cited

U.S. PATENT DOCUMENTS

| | | | |
|---|---|---|---|
| 6,641,553 B1 * | 11/2003 | Chee | A61B 17/32037 604/68 |
| 7,918,787 B2 | 4/2011 | Saadat | |

(Continued)

FOREIGN PATENT DOCUMENTS

WO 2011022069 A2 2/2011

OTHER PUBLICATIONS

Sharma et al; "Early identification of haemodynamic response to pharmacotherapy is essential for primary prophylaxis of variceal bleeding with high-risk varices", Aliment. Pharmacol. Ther. vol. 30, pp. 48-60, (2009).

(Continued)

*Primary Examiner* — Andrew Yang
(74) *Attorney, Agent, or Firm* — Seager, Tufte & Wickhem, LLP (57) ABSTRACT

The present disclosure relates to the field of endoscopy. Specifically, the present disclosure relates to delivery systems and methods for coagulating sites of bleeding within mucosal tissues, and in particular, for eradicating esophageal varices.

20 Claims, 5 Drawing Sheets

(51) Int. Cl.
   *A61B 17/00*     (2006.01)
   *A61B 18/00*     (2006.01)

(56) References Cited

U.S. PATENT DOCUMENTS

2009/0281429 A1* 11/2009 Nishina .................. A61B 8/445
                                                    600/459
2011/0166561 A1    7/2011 Coluccia et al.

OTHER PUBLICATIONS

Viviane et al; "Estimates of costs of hospital stay for variceal and nonvariceal gastrointestinal bleeding in the United States," Value in Health, vol. 11 No. 1, pp. 1-3 (2008).

Petrasch, et al; "Differences in bleeding behavior after endoscopic band ligation: a retrospective analysis," BMC Gastroenterology, 10:5, pp. 1-10 (2010).

Hou et al; "Comparison of endoscopic variceal injection sclerotherapy and ligation for the treatment of esophogeal variceal hemorrhage: A prospective randomized trial," Hepatology vol. 21, pp. 1157-1522, 1995.

Masalaite et al; "Recurrance of esophogeal varices after endoscopic band ligation: single centre experience," Acta Medica Lituanica. vol. 19, No. 2, pp. 59-66 (2012).

Scaglione et al; "The Epidemiology of Cirrhosis in the United States: A Population-based Study," J. Clin. Gastoenterol; vol. 49, No. 8, pp. 690-696, (2015).

Kochaneck et al; "Deaths: Final Data for 2014," National Vital Statistics Reports, Chronic Liver Disease and Cirrhosis Mortality Rates, U.S. Center for Disease Control and Prevention, vol. 65, No. 4 pp. 1-121 (2016).

Sarin et al; "Prevalence, classification and natural historyof gastric varices: A long term follow-up study in 568 portal hypertension patients," Hepatology 16 1343-1349 (1992).

Augustin et al; "Acute esophogeal variceal bleeding : Current strategies and new perspectives," World J. Hepatol. vol. 2, No. 7, pp. 261-274 (2010).

Dai et al; "Endoscopic variceal ligation compared with endoscopic injection sclerotherapy for treatment of esophageal variceal hemorrage: A meta-analysis." World J. Gastoenterol, vol. 28, No. 21(8), pp. 2534-2541 (2015).

* cited by examiner

SYSTEM AND METHOD FOR TREATMENT OF GASTROESOPHAGEAL VARICES

CROSS-REFERENCE TO RELATED APPLICATIONS

This application is a continuation of Ser. No. 15/638,474, filed Jun. 30, 2017, which claims the benefit of U.S. Provisional Application No. 62/357,598, entitled "SYSTEM AND METHOD FOR TREATMENT OF GASTROESOPHAGEAL VARICES" and filed Jul. 1, 2016, which is hereby incorporated by reference in its entirety.

FIELD

The present disclosure relates to the field of endoscopy. Specifically, the present disclosure relates to systems and methods for coagulating sites of bleeding within tissues such as mucosal tissues, and in particular, for eradicating esophageal varices.

BACKGROUND

Gastroesophageal varices develop when normal blood flow to the liver is obstructed by scar tissue caused by cirrhosis. The scar tissue forces blood into smaller vessels surrounding the esophagus or stomach, causing the vessels to swell, leak and eventually rupture. Approximately 80 percent of patients with cirrhosis develop varices of the esophagus, and approximately 17 percent develop gastric varices (*Hepatology*, 16, 1343-49 (1992)). Bleeding occurs in approximately 36 percent of patients and is associated with a mortality rate of at least 20 percent, which increases to 50 percent with each bleeding episode. In the United States alone, gastroesophageal varices due to cirrhosis account for more than 25,000 deaths and 373,000 hospitalizations annually (*J. Clin. Gastroenterol.*, (2014); *U.S. Center for Disease Control and Prevention*, (2014)).

The primary prophylactic treatment for variceal bleeds is non-selective beta-blockers that reduce portal hypertension. Studies have shown that beta-blockers are only effective in 38 percent of patients (*Aliment. Pharmacol. Ther.*, 30, 48-60 (2009)). Application of cyanoacrylate glue (Covidien, TissueSeal and Ethicon) into gastroesophageal varices has been shown to eliminate bleeds, however, the glue has a limited working time after mixing and poses a risk of systemic embolization.

Endoscope band ligation may be used to treat acute bleeds or when non-selective beta-blockers have failed. Unfortunately, band ligation can have a number of drawbacks, including high cost, low efficacy and various safety concerns. Significant training is required to deliver the bands in a controlled manner. Furthermore, the bulge that forms when a varix is banded may obscure the field of view, which may limit the ability to maneuver the endoscope and may make subsequent band placements more difficult. As the number of deployed bands increases, the likelihood of the endoscope accidentally dislodging a band and causing a bleed increases. These factors may limit the number of bands that can be deployed to approximately 6 per session. On average, 2-4 procedures may be required to eradicate all of the varices. These treatments may be expensive and may increase the risk of acute bleeds occurring from varices that are awaiting treatment. These untreated bleeds may be associated with a four-fold increase in hospital costs, including possibly increased hospitalization times (*Value Heal.*, 11, 1-3 (2008)). Ulcers and strictures also may tend to form in the mucosal lining of the esophagus when the bands slough off. Some studies have shown that more than 12 percent of patients experience re-bleeding after a band ligation procedure (*BMC Gastroeneterol.*, 10, 1-10 (2010)). The average band ligation procedure may take more than 50 days to complete, with varices possibly recurring in up to 75 percent of patients after two years. Some studies claim that these re-bleeds are estimated to result in a four-fold increase in both the duration of hospitalization and treatment costs (*Value Heal.*, 11, 1-3 (2008)).

The risks and costs that may be associated with existing endoscope banding treatments may be too high to warrant earlier intervention to prevent recurrence of varices and bleeds (*Hepatology* 21, 1517-1522 (1955); *ACTA Medica. Litu.*, 19, 59-66 (2012). There is an ongoing need for an easier-to-use and more cost-effective system capable of coagulating multiple varices in a single procedure without damaging surrounding mucosal tissues.

SUMMARY

The present disclosure, in its various aspects, meets an ongoing need in the medical field, such as the field of surgical endoscopy, for a system that utilizes high intensity focused ultrasound to eradicate multiple gastroesophageal varices in a single procedure while minimizing damage to surrounding mucosal tissues.

In one aspect, the present disclosure relates to an endoscope cap, comprising a proximal portion; a distal portion; a lumen extending between the proximal and distal portions; and an ultrasound transducer array disposed at the distal portion and configured to direct ultrasonic energy into the lumen. The ultrasound transducer array may be configured to direct high intensity focused ultrasound into the lumen of the endoscope cap at a fixed angle. The ultrasound array may be at least partially embedded within a wall of the endoscope cap. At least a distal portion of the endoscope cap may be made from a substantially transparent material.

In another aspect, the present disclosure relates to a device, comprising an endoscope cap configured to be coupled to the distal end of an endoscope. The endoscope cap may include a proximal portion; a distal portion; a lumen extending between the proximal and distal portions; a power cable extending along the endoscope cap; and an ultrasound transducer array electrically connected to the power cable, the ultrasound transducer array configured to direct high intensity focused ultrasound into the lumen. The power cable may extend along an inner or outer surface of the endoscope cap. In addition, or alternatively, the power cable may be at least partially embedded within a wall of the endoscope cap. In addition, or alternatively, the power cable may be at least partially disposed in a groove within an inner wall of the endoscope cap. The distal end of the endoscope may be disposed within the lumen of the proximal portion of the endoscope cap. The endoscope may include at least one working channel in communication with the lumen of the endoscope cap. The at least one working channel may be connected to a suction source. In addition, or alternatively, the endoscope may include first and second working channels, wherein the first working channel may be connected to a suction source, and the second working channel may be connected to a coolant source. The distal end of the endoscope may include a camera and/or a light source.

In yet another aspect, the present disclosure relates to a method of treating a tissue, comprising: a) positioning an endoscope cap that includes a source of high intensity focused ultrasound configured therein at a location of target tissue in a body lumen of a patient; b) positioning the endoscope cap over the surface of the target tissue; c) drawing the target tissue into the lumen of the endoscope cap; and d) delivering high intensity focused ultrasound to the target tissue. The method may further include introducing a coolant into the lumen of the endoscope cap prior to, or during, delivery of the high intensity focused ultrasound to the target tissue. The method may further include the additional steps of e) releasing the tissue from the lumen of the endoscope cap; f) repositioning the endoscope cap over the surface of a second target tissue and repeating steps a), b), c) and d). The target tissue may include a gastroesophageal varix. The high intensity focused ultrasound may coagulate at least a portion of the blood within the gastroesophageal varix.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Before the present disclosure is described in further detail, it is to be understood that the disclosure is not limited to the particular embodiments described, as such may vary. It is also to be understood that the terminology used herein is for the purpose of describing particular embodiments only, and is not intended to be limiting beyond the scope of the appended claims. Unless defined otherwise, all technical terms used herein have the same meaning as commonly understood by one of ordinary skill in the art to which the disclosure belongs. Finally, although embodiments of the present disclosure are described with specific reference to systems and methods for coagulation of gastroesophageal varices, it should be appreciate that the system of the present disclosure may be used to promote sub-surface coagulation within a number of tissue surfaces or layers, such as mucosal tissues, including, for example, the rectum, vagina, intestines, larynx and stomach etc. It should also be appreciated that the endoscope cap is not limited to use with an endoscope, but may be attached to a variety of medical devices such as laparoscopes, colonoscopes, ureteroscopes and the like.

As used herein, the term "distal" refers to the end farthest away from a medical professional when introducing a device into a patient, while the term "proximal" refers to the end closest to the medical professional when introducing a device into a patient.

As used herein, the term "varix," or "varices" (plural) refers to an abnormally dilated vessel that typically includes a tortuous shape. Varices tend to occur in the venous system, but may also occur in the arterial or lymphatic systems. Examples of varices include, varicose veins, sublingual varices, esophageal varices, gastric varices, intestinal varices, scrotal varices, vulvar varices, vesical varices (i.e., varices associated with the urinary bladder) and rectal varices.

Figure 1A:
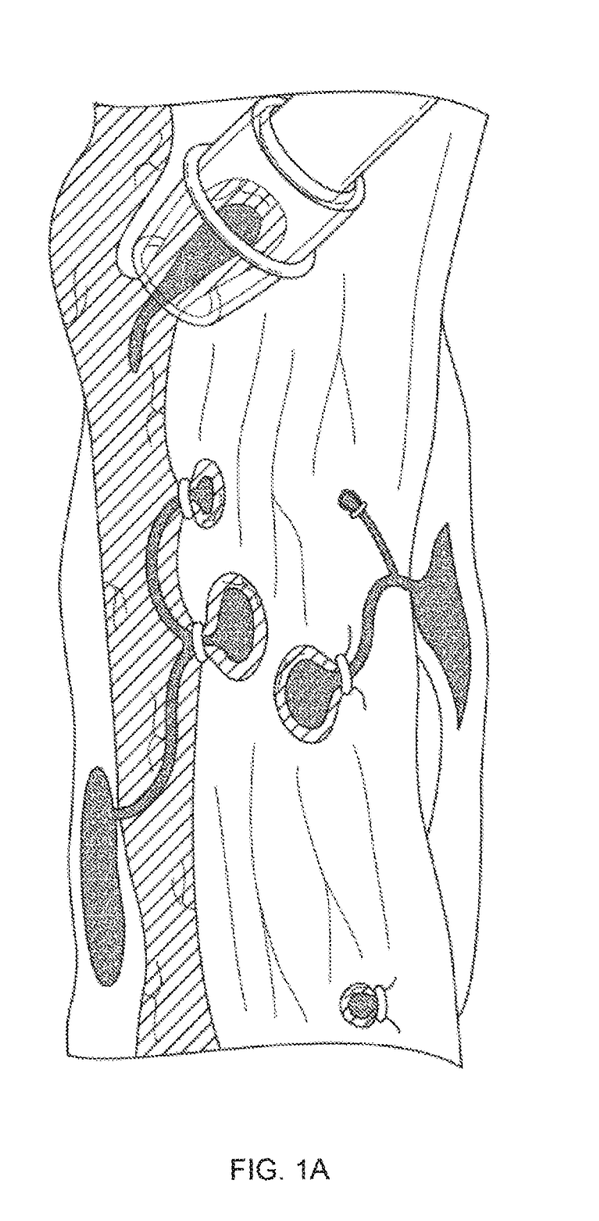
FIGS. 1A-1C illustrate endoscope band ligation procedures (FIGS. 1A and 1B) and a magnified view of an endoscope band disposed around an esophageal varix (FIG. 1C).
Figure 1B:
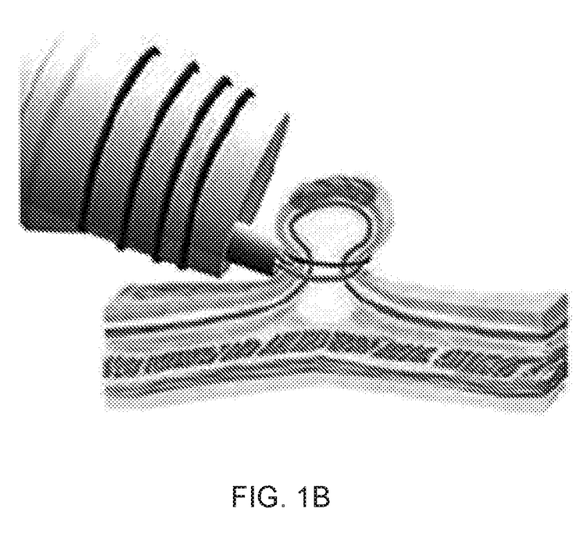
Figure 1C:
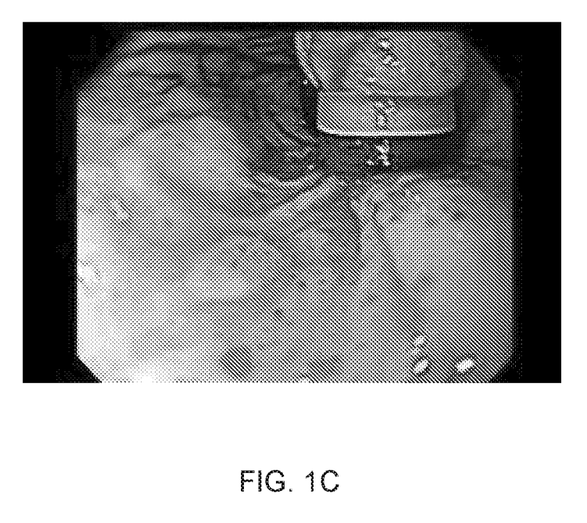
Figure 2A:
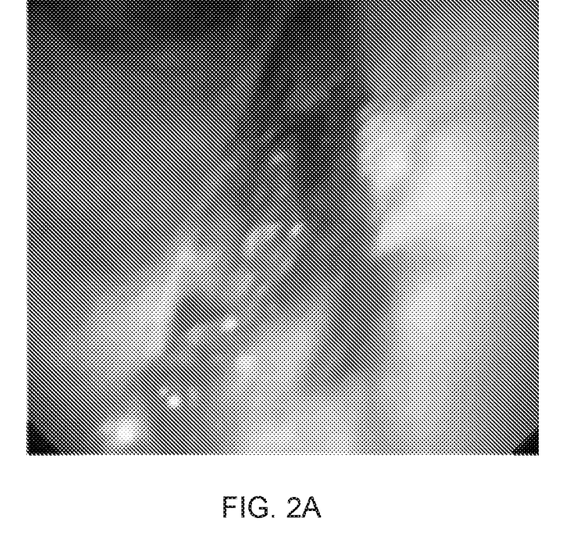
FIGS. 2A-2B illustrate ulcers formed in the esophageal mucosa following an endoscope band ligation procedure.
Figure 2B:
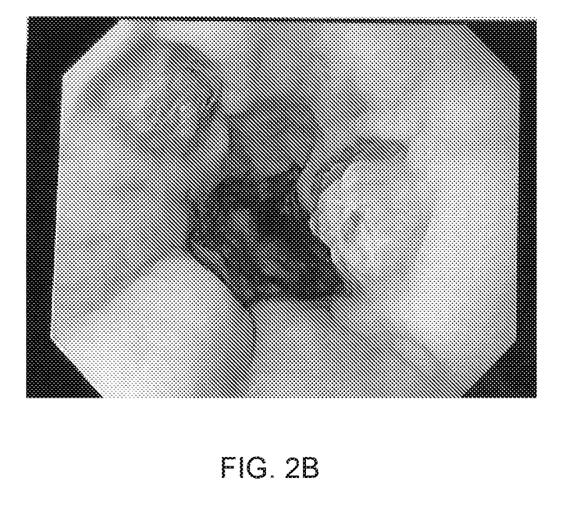

Current treatment of gastroesophageal varices is carried out using a transparent cap mounted on an endoscope via a process known as endoscope variceal ligation. As illustrated in FIG. 1A, the medical professional suctions a target varix into the endoscope cap, and deploys a rubber band to occlude the flow of blood through the varix (FIG. 1C). An alternative gastroesophageal variceal ligation procedure may include using a snare disposed on the distal end of an endoscope to gather the target tissue (FIG. 1B) and deploying a rubber band as discussed above. Necrosis occurs in the tissues around the banding, causing it to slough off over time, and leaving behind in some cases an ulcerated area that may result in stricture formation (FIGS. 2A-2B).

In one embodiment, the present disclosure provides an endoscope system that uses a high intensity focused ultrasound (HIFU) transducer array to locally heat and coagulate sub-surface varices. This is unlike other tissue heating modalities, such as radiofrequency (RF) energy, laser energy or plasma energy, which deliver thermal energy from the tissue surface inward, resulting in heating from the device inward and in some cases to "charring" or "burning" throughout the tissue. By comparison, HIFU energy applied in the 5-12 MHz range establishes localized "hotspots" within the lumen of an endoscope cap that coagulate, rather than cauterize, the blood within a varix with minimal heating of surrounding tissues. Cooling fluid may be applied to the tissue surface through a working channel of the endoscope to further minimize tissue injury that may result in ulcerations and re-bleeding.

Figure 3:
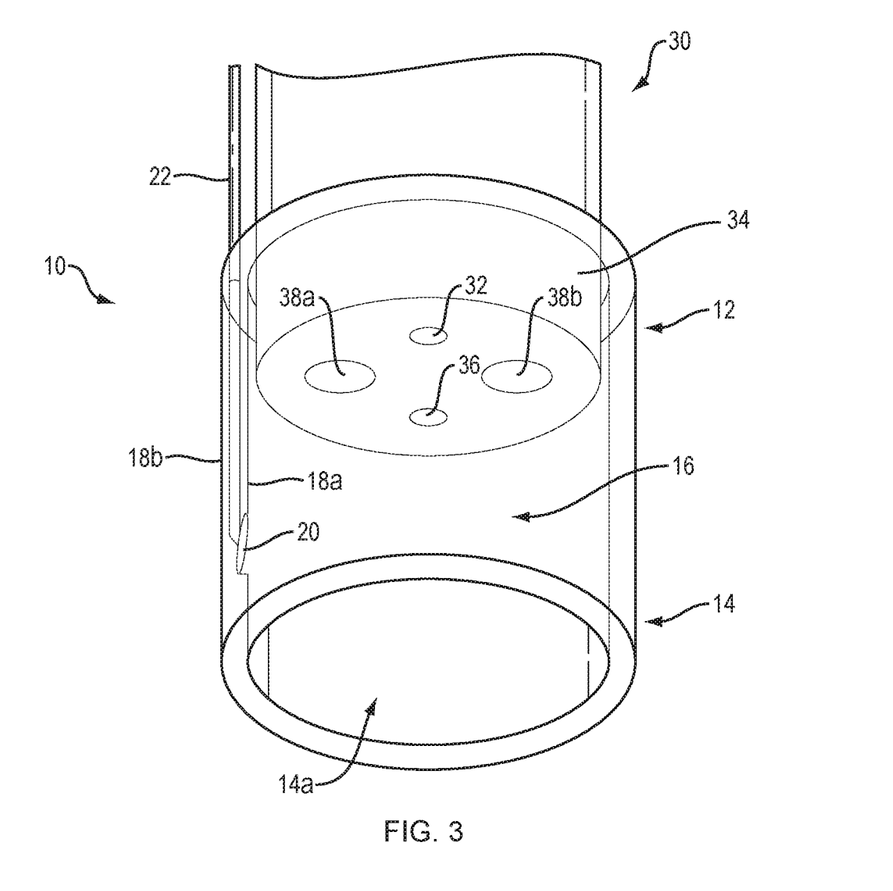
FIG. 3 illustrates an endoscope cap disposed on the distal end of an endoscope, in accordance with an embodiment of the present disclosure.

FIG. 3 illustrates a HIFU transducer array 20 integrated within an endoscope cap 10, according to one embodiment of the present disclosure. To facilitate positioning within a patient, the endoscope cap 10 is preferably substantially cylindrical and includes a proximal portion 12, distal portion 14 and a lumen 16 (i.e., working channel) extending therebetween. The lumen 16 is defined by an inner surface 18a with a preferably substantially constant inner diameter. The distal portion 14 defines an opening 14a configured to permit soft tissues to be drawn into the lumen 16 using endoscope suction. The HIFU transducer array 20 is positioned at a fixed angle along the inner surface 18a of the endoscope cap 10 to direct a spherically focused beam of high intensity ultrasound into the center of the lumen 16 with sub-millimeter precision. In one embodiment, the HIFU transducer array is at least partially embedded within the inner surface 18a of the endoscope cap 10. The HIFU transducer array may be connected to an external power supply (not depicted) by a coaxial cable 22 extending along a length of the endoscope cap. The coaxial cable 22 depicted in FIG. 3 is embedded within the wall of the endoscope cap 10. In other embodiments, the coaxial cable may be disposed in a groove formed within the inner surface 18a or outer surface 18b of the endoscope cap 10. In one embodiment, the angle of the HIFU transducer array may be configured to provide multiple overlapping energy fields within the lumen of the endoscope cap. In another embodiment, multiple HIFU transducer arrays may be configured to provide multiple overlapping energy fields within the lumen of the endoscope cap. As will be understood by those in the art, such overlapping energy fields increase heating of tissues by $N^2$, where N is the number of energy fields applied. One of ordinary skill in the art will appreciate that the degree of offset of a multiple transducer array is contingent on the number of arrays required and may be set at 180° assuming two arrays, at 120° assuming 3 arrays and so on. In another embodiment, the application of differing media within the cap could be used to initiate a variable acoustic output. Media such as water, saline, air etc. can be employed.

Still referring to FIG. 3, the proximal portion 12 of the endoscope cap 10 is dimensioned to receive the distal end 34 of an endoscope 30. The endoscope cap 10 may be designed to either permanently or temporarily attach to the distal end 34 of the endoscope 30. Permanent attachment mechanisms may include gluing, welding, soldering or the like, while temporary locking mechanisms may include a snap-fit, screw-fit, luer-lock, press-fit or interference fit using a silicone component or similar device formed into the endoscope cap 10. The endoscope 30 may include a light source 32 and camera 36 to allow the medical professional to visualize the esophageal tissue and identify target varices. As discussed below, the endoscope 30 may further include one or more working channels 38a, 38b through which a suction may be drawn or coolant delivered.

Figure 4A:
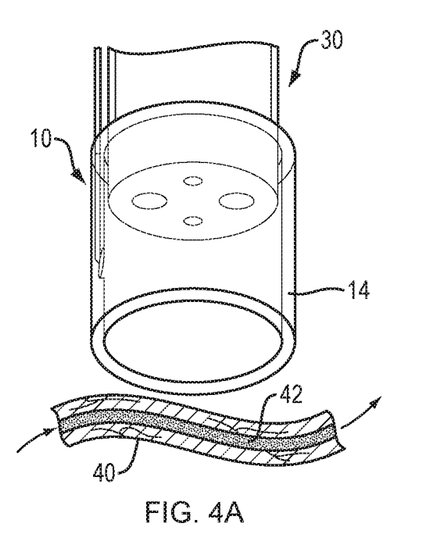
FIGS. 4A-4D illustrate the steps involved in coagulating an esophageal varix using high intensity focused ultrasound, in accordance with an embodiment of the present disclosure.
Figure 4B:
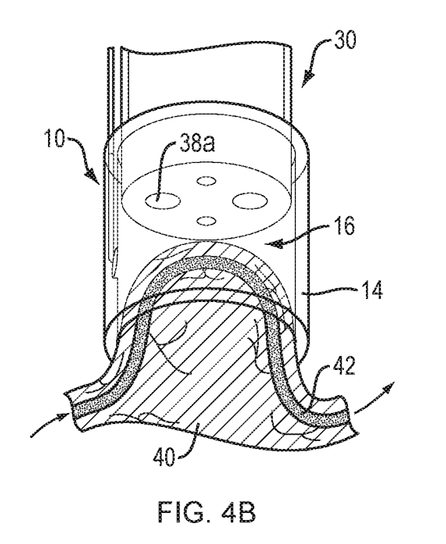
Figure 4C:
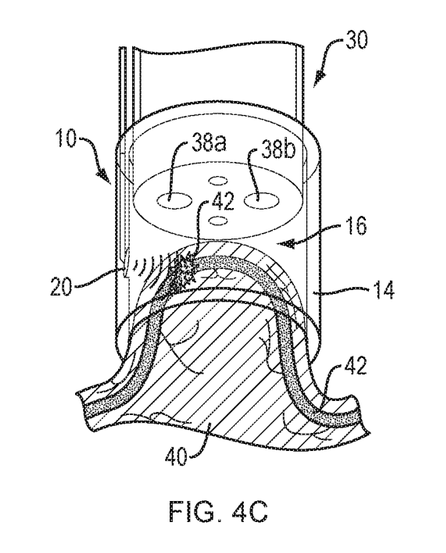
Figure 4D:
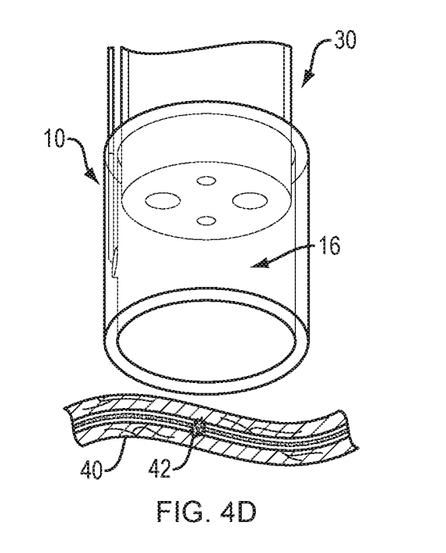

FIGS. 4A-4D illustrate the use of the endoscope cap 10 of FIG. 3 in performing a gastroesophageal varix coagulation procedure. A medical professional may introduce the endoscope cap 10 attached to the distal end 34 of an endoscope 30 into a patient's esophagus. Referring to FIG. 4A, the distal portion 14 of the endoscope cap 10 is positioned over and in contact with the mucosal layer of a target tissue 40 that includes a varix 42. Referring to FIG. 4B, the medical professional applies suction through the first working channel 38a of the endoscope 30 to draw the target tissue 40 and varix 42 into the lumen 16 of the endoscope cap 10. The force of the suction is sufficient to isolate the varix 42 from surrounding tissue and effectively slow the flow of blood, thereby minimizing the heat sink effect of circulating blood. Trapping the varix 42 within the lumen 16 also stabilizes the varix within the center of the endoscope cap 10 to ensure accurate delivery of the high intensity focused ultrasound. Referring to FIG. 4C, with the suction source maintaining the varix 42 within the lumen 16 of the endoscope cap 10, the medical professional activates the HIFU transducer array 20 to deliver a focused pulse of high energy ultrasound into the varix 42. The high intensity focused ultrasound is typically applied for less than 10 seconds to coagulate the blood trapped within the varix 42. Shorter or longer pulses of high intensity focused ultrasound may be applied at the discretion of the medical professional. Coolant (not depicted) may be introduced into the lumen 16 of the endoscope cap 10 through a second working channel 38b of the endoscope 30 to further minimize heating of the tissue, such as mucosal tissue, surrounding the varix 42, thereby reducing the risk of tissue damage that may result in post-procedure ulcerations and/or re-bleeding. Referring to FIG. 4D, once the blood flowing through the varix 42 is coagulated, the medical professional may release the suction such that the target tissue 40 is released from the lumen 16 of the endoscope cap 10. The medical professional may then withdraw the endoscope from the patient. Alternatively, the medical professional may reposition the distal portion 14 of the endoscope cap for treatment of additional varices, including small varices that may be unsuitable for ligation banding, by repeating the steps outlined above.

It should be appreciated the dimensions of the endoscope 30 and endoscope cap 10 may vary according to a variety of factors, include the desired application and size of the patient. For example, an endoscope cap designed for rectal insertion may be considerably smaller than an endoscope cap designed for insertion into the esophagus. To further enhance visualization, at least a portion of the endoscope cap may be formed from a transparent or translucent material, such as a clear polymer-based material (i.e., clear plastics, etc.) as are known in the art. The endoscope cap may be designed for multiple or single uses. As a single-use device, for example, the endoscope cap may include a temporary attachment mechanism and may be stored in hermetically sealed, sterile packaging before use. A multiple-use device, however, may be designed of materials able to withstand high temperature and high pressure sterilization conditions such as those provided by an autoclave.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An endoscope cap, comprising:
   a proximal portion;
   a distal portion;
   a lumen extending between the proximal and distal portions, the lumen configured to accept drawn in tissue; and
   an ultrasound transducer array disposed at the distal portion and configured to direct ultrasonic energy into the lumen.

2. The endoscope cap of claim 1, wherein the ultrasound transducer array is configured to direct high intensity focused ultrasound into the lumen of the endoscope cap at a fixed angle.

3. The endoscope cap of claim 1, wherein at least a distal portion of the endoscope cap is made from a substantially transparent material.

4. A device, comprising:
   an endoscope cap configured to be coupled to a distal end of an endoscope, the endoscope cap including:
   a proximal portion;
   a distal portion;
   a lumen extending between the proximal and distal portions, the lumen configured to accept drawn in tissue;
   a power cable extending along the endoscope cap; and
   an ultrasound transducer array electrically connected to power cable, the ultrasound transducer array configured to direct high intensity focused ultrasound into the lumen.

5. The device of claim 4, wherein the power cable extends along an inner surface of the endoscope cap.

6. The device of claim 4, wherein the power cable extends along an outer surface of the endoscope cap.

7. The device of claim 4, wherein the power cable is at least partially embedded within a wall of the endoscope cap.

8. The device of claim 4, wherein the power cable is at least partially disposed in a groove within an inner wall of the endoscope cap.

9. The device of claim 4, wherein the distal end of the endoscope is disposed within the lumen of the proximal portion of the endoscope cap.

10. The device of claim 4, wherein the endoscope includes at least one working channel in communication with the lumen of the endoscope cap.

11. The device of claim 10, wherein the at least one working channel is connected to a suction source.

12. The device of claim 4, wherein the endoscope includes first and second working channels, wherein the first working channel is connected to a suction source, and wherein the second working channel is connected to a coolant source.

13. The device of claim 4, wherein the distal end of the endoscope includes a camera.

14. The device of claim 4, wherein the distal end of the endoscope includes a light source.

15. An endoscope cap, comprising:
a proximal portion;
a distal portion;
a lumen extending between the proximal and distal portions, the lumen configured to accept drawn in tissue;
an inner surface of the proximal portion and the distal portion extending along the lumen; and
an ultrasound transducer array disposed within the inner surface.

16. The endoscope cap of claim 15, wherein the ultrasound transducer array is disposed at the distal portion and is configured to direct ultrasonic energy into the lumen.

17. The endoscope cap of claim 15, wherein the ultrasound transducer array is configured to direct high intensity focused ultrasound into the lumen of the endoscope cap at a fixed angle.

18. The endoscope cap of claim 15, wherein the proximal portion of the endoscope cap is configured to be disposed about an endoscope having a working channel, and wherein the lumen is in fluid communication with the working channel.

19. The endoscope cap of claim 18, wherein the working channel is in fluid communication with a suction source.

20. The endoscope cap of claim 15, wherein the ultrasound transducer array is configured to direct high intensity focused ultrasound substantially toward a central axis of the lumen of the endoscope cap.

* * * * *